(12) United States Patent
Holliday

(10) Patent No.: US 9,433,753 B2
(45) Date of Patent: Sep. 6, 2016

(54) MEDICAL TUBING STABILIZER

(76) Inventor: Barbara R. Holliday, Brattleboro, VT (US)

(*) Notice: Subject to any disclaimer, the term of this patent is extended or adjusted under 35 U.S.C. 154(b) by 1239 days.

(21) Appl. No.: 13/185,460

(22) Filed: Jul. 18, 2011

(65) Prior Publication Data

US 2012/0016310 A1 Jan. 19, 2012

Related U.S. Application Data

(60) Provisional application No. 61/365,245, filed on Jul. 16, 2010.

(51) Int. Cl.
*A61M 25/00* (2006.01)
*A61M 25/02* (2006.01)
*A61M 5/14* (2006.01)

(52) U.S. Cl.
CPC ............ *A61M 25/02* (2013.01); *A61M 5/1418* (2013.01); *A61M 2025/0266* (2013.01); *A61M 2205/04* (2013.01)

(58) Field of Classification Search
CPC ......... A61M 2025/026; A61M 25/02; A61M 2025/0253; A61M 2025/0266

USPC .......................................... 604/174, 178–180
See application file for complete search history.

(56) References Cited

U.S. PATENT DOCUMENTS 6,689,105 B2 * 2/2004 Tollini ........................ 604/180

* cited by examiner

*Primary Examiner* — Bhisma Mehta
*Assistant Examiner* — Bradley Osinski

(57) ABSTRACT

In various embodiments of the invention, a system and dynamic device are provided to create stability of tube placement in medical and other applications. The described systems and principles also apply in other environments outside of medicine and healthcare. The described medical tubing stabilizer adheres to the tubing itself providing handles or anchors to prevent stitch slippage and to prevent the tubing from falling out in any situation that requires a semi or permanent tubing placement. The device also aides in stabilizing the tubing in the wound site, and thus maximizes placement in its intended area of effect (e.g., in the body cavity, in a medical context). These stabilizing effects substantially minimize slippage of stitching holding the tubing in place to prevent the tubing from falling out or becoming dislodged or displace, thus preventing irritation and damage to the skin around the wound site, infection, seroma, edema and morbidity in a medical context.

7 Claims, 5 Drawing Sheets

MEDICAL TUBING STABILIZER

CROSS-REFERENCE TO RELATED APPLICATIONS

This patent application claims the benefit of U.S. Provisional Patent Application No. 61/365,245 filed Jul. 16, 2011, which is herein incorporated by reference in its entirety for all that it shows, describes, and teaches, without exclusion of any portion thereof.

BACKGROUND OF THE INVENTION

In the medical field, it is often necessary to use tubing to provide a fluid pathway for drainage, medication, aeration, etc. However, even in critical applications, there is the risk that the tubing that has been inserted into a body location may migrate or dislodge, resulting in a lack of proper function. In some situations, in addition to failure to provide the function for which it was inserted, the dislodged tubing may actually lacerate or otherwise damage other body elements.

Acute complications from tube migration or dislodgement include laceration of intercostals vessel (may require thoracotomy), lung laceration, diaphragm/abdominal cavity penetration (placed too low), stomach/colon injury (diaphragmatic hernia not recognized), tube placed subcutaneously (not in thoracic cavity), tube placed too far (pain), tube falls out (not secured), and others.

The following references describe various issues and complications caused by tube migration or dislodgement:

MATTOX, K L, et al., "Systematic Approach to Pneumothorax, Haemothorax, Pneumomediastinum and Subcutaneous emphysema", *Injury,* 1986; 17:309-312, Symposium paper.

ETOCH, S W, et al., "Tube Thoracostomy, Factors Relating to Complications", *Archives of Surgery,* 1995; 130:521-525.

MILIKAN, J S, et al., "Complications of Tube Thoracostmy for Acute Trauma", *AM J. Surgery.* 1980; 140:738-741.

BAILEY, R C., "Complications of Tube Thoracostomy in Trauma," J *Accid Emerg Med.* 2000; 17:111-114.

Thus, there is a need for a tubing affixing system in the medical context that allows a care provider or patient to ensure that a tube that has been accurately placed in a body cavity or opening remains properly fixed and located.

BRIEF SUMMARY OF THE INVENTION

The invention provides a medical tubing stabilizer. The medical tubing stabilizer's purpose is to create stability of tube placement in an unstable environment. While one primary use is to secure tubing in a medical procedure or in a medical context, the described systems and principles also apply in other environments outside of medicine and healthcare.

The described medical tubing stabilizer is a dynamic tool that adheres to the tubing itself providing extra strong handles or anchors to prevent stitch slippage and to prevent the tubing from falling out in any situation that requires a semi or permanent drainage, or other-purpose, tubing. The device also aides in stabilizing the tubing in the wound site, and thus maximizes placement in its intended area of effect (e.g., in the body cavity, in a medical context). These stabilizing effects substantially minimize slippage of stitching holding the tubing in place to prevent the tubing from falling out or becoming dislodged or displaced, thus preventing irritation and minimizing damage to the skin around the wound site, infection, seroma, edema and morbidity in a medical context.

DETAILED DESCRIPTION OF THE INVENTION

In a preferred embodiment of the invention, the described device is manufactured as a flat piece that is folded around the tube and secured by use of two snap cap closures, thus ensuring a tight fit to the tube it is designed to secure. However, other implementations are also possible within the described principles, e.g., producing the device as an extruded tube to be slid over the tube to be secured, producing the tubing to be secured with the device as a part of it. Moreover, various closure types are possible, some of which will be described herein and others of which will become apparent to those of skill in the art upon reading this disclosure. Thus, the following describes preferred embodiments, but is not intended to limit the invention to those embodiments only.

Figure 1:
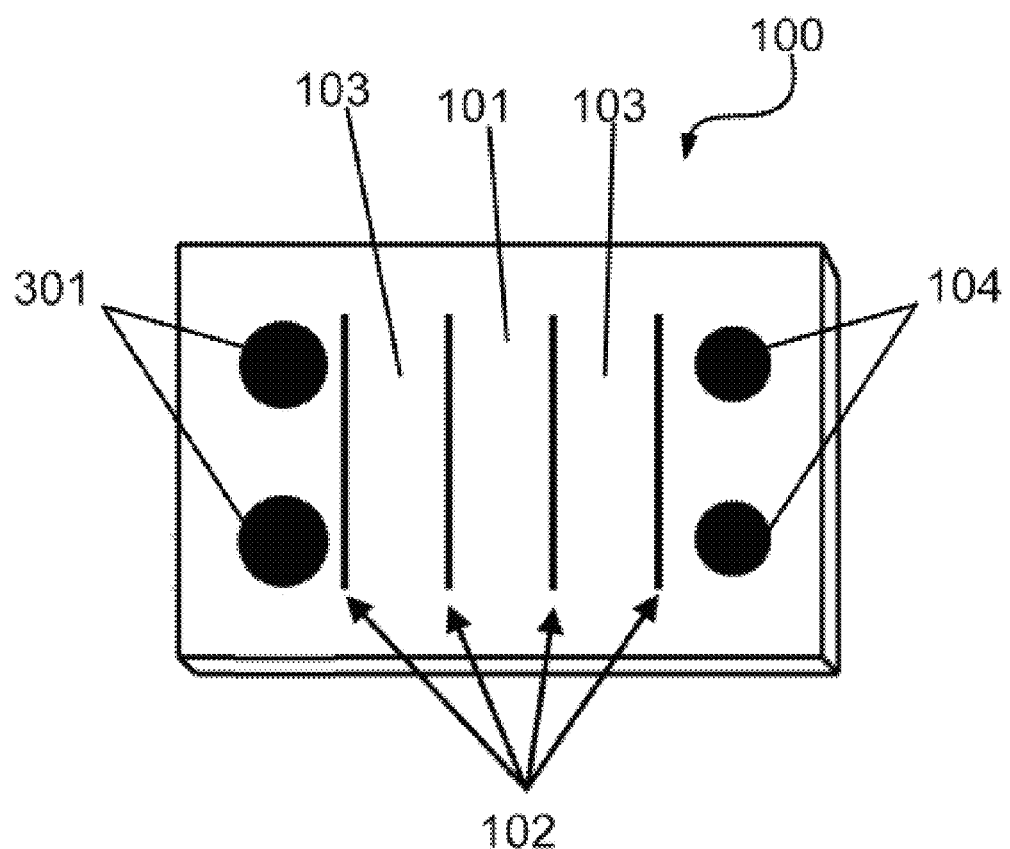
FIG. 1 is a schematic top view of a medical tubing stabilizer according to an embodiment of the invention showing anchor handles, and the dimensions of the four reinforced openings that construct the two handles.

As noted above, FIG. 1 is a top and outside view of a medical tubing stabilizer in accordance with an embodiment of the invention. In the illustrated embodiment of the invention, the stabilizer 100 has a 0.75 inch width by 1.5/32 inch length, although it will be appreciated by those of skill in the art that any suitable size may be used instead. The stabilizer body is made of a suitably high tensile strength material, e.g., medical grade rubber, elastic, and so on in various embodiments of the invention.

The device 100 includes a solid middle portion 101 (0.125 inch on either side of center in the illustrated embodiment of the invention, creating a solid middle piece ⅜ inch wide). On either side of the centered middle piece 101, two centered cuts 102 from top to bottom, four in total, are created on the device 100. In an embodiment of the invention, the cuts 102 are ¹⁰⁄₃₂ inch long, although the exact length is not important. Further in the illustrated embodiment of the invention, the two cuts in each pair (four in total) are spaced at ⅜ inches apart. These openings create the outside anchor handles 103.

Figure 2:
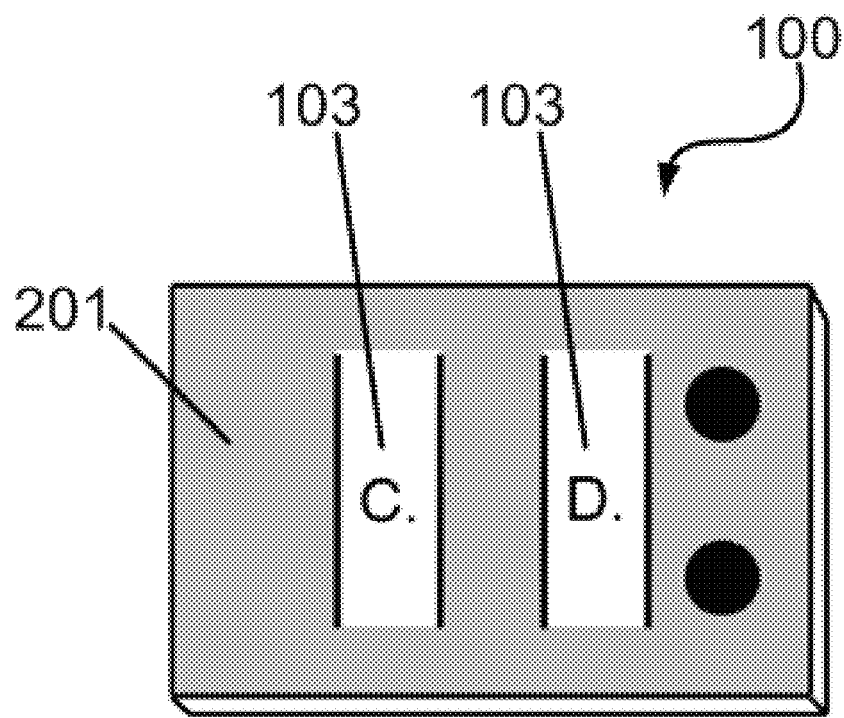
FIG. 2 is a schematic under or inside view of the medical tubing stabilizer according to an embodiment of the invention, showing areas of adhesive application.

FIG. 2 shows the area 201 of application of adhesive in an embodiment of the invention. In this embodiment, the device 100 wraps around the object to be stabilized (e.g., tubing) as an adhesive strip, with the adhesive areas 201 grasping the tubing as the non adhesive solid pieces 103 bend outward to create the anchor handles as will be shown more explicitly in later drawings. In an embodiment of the invention, the anchor openings may be reinforced with a lining, e.g., a 1/32 inch layer of rubber (not shown), molded 360° around the interior of the openings. The centered cuts begin 4/32 inch from the exterior wall lengthwise on either side of the device 100 inwards in a further embodiment of the invention.

There are portions of Velcro® molded onto either end of the rubber piece in an embodiment, e.g., 5/8 inch pieces with one on the top or outside the non adhesive side and one on the adhesive inside of the rubber body, at the opposite end so as to mate when the device 100 is wrapped around a tube or other suitably sized object.

Figure 3:
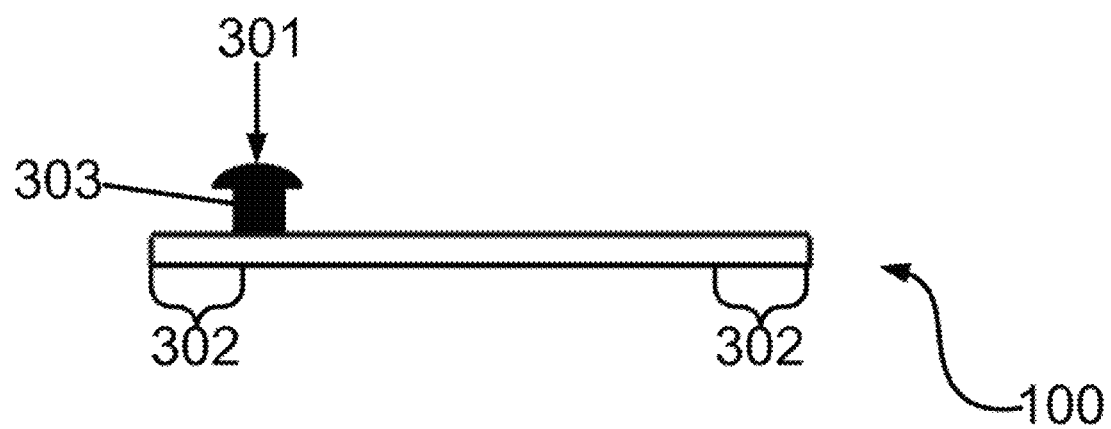
FIG. 3 is a schematic side view of the medical tubing stabilizer according to an embodiment of the invention showing a cross-section of a fastener with locking cap.

Referring now to FIG. 3, in a further embodiment, the adhesive top of the rubber body may have snap cap fasteners 301 with an interlocking lip 302 nested in the Velcro®. There are holes or openings at the opposite end (not shown in side view, but shown as holes 104 in FIG. 1) that lift up and over the snap caps 301, joining the two ends of the body of the device after it is wrapped tightly around and adhered to the object it is grasping.

In an embodiment of the invention, the snap cap fasteners 301 each consist of a rubber stem (303), e.g., 4 mm in height and 4 cm in diameter. The cap or top has an overhang of 0.5 cm around the circumference with a separate crescent shaped lip extension on the side of the fastener cap extending 1.5 cm (facing inward where the device sustains the most pressure to release) locking the device in place, i.e., in this embodiment of the invention, the snap cap 302 top is not entirely symmetrical, but is extended to provide a large overhang in the direction retaining the holes 104 when the device is wrapped. This is referred to herein as a snap cap with interlocking lip.

Figure 4:
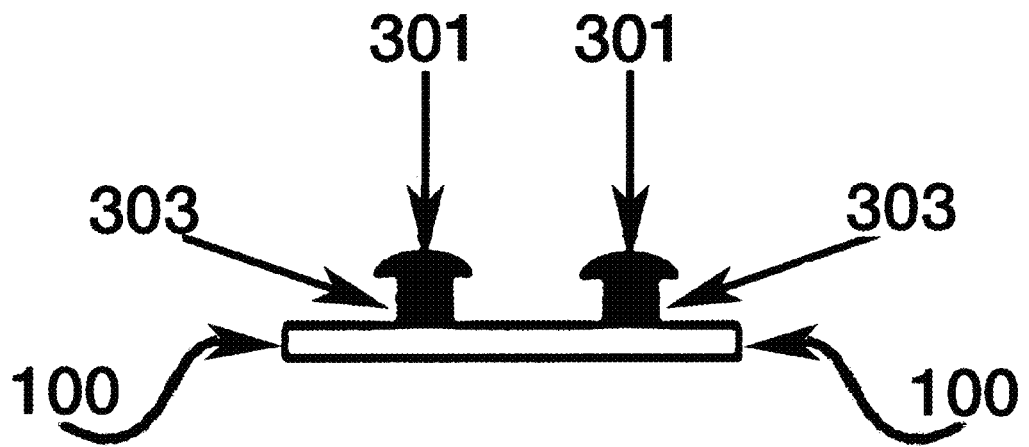
FIG. 4 is a schematic end view of the medical tubing stabilizer according to an embodiment of the invention showing two fasteners and locking caps.

The device 100 is shown in an end-on side view in FIG. 4. The pair of snap caps 301 and their respective stems 303 can be seen. It will be appreciated that although a pair of snap caps is shown, the described principles may be applied with one or no snap caps, or with a greater number, i.e., 3, 4, etc. depending upon manufacturer preferences, budget, size, etc.

In general, the device 100 is strong, flexible to fit to size, adaptable in environments where movement is a factor, creates elastic handles to connect and secure a wide variety of tubing and other items in surgical, emergency medical events, training and teaching and other environments that need a dynamic tool to adapt to any situation in a non static way. The adhesive inside, with peel off backing creates an ease of delivery around any property needing stabilization.

There are four tiers of security provided in various embodiments of the invention, namely the adhesive inside, the reinforced anchor handles, the Velcro® attachments, the snap caps, and the overlocking lips. It will be appreciated that these improvements may be used together in various combinations or singly as the need may be.

Figure 5:
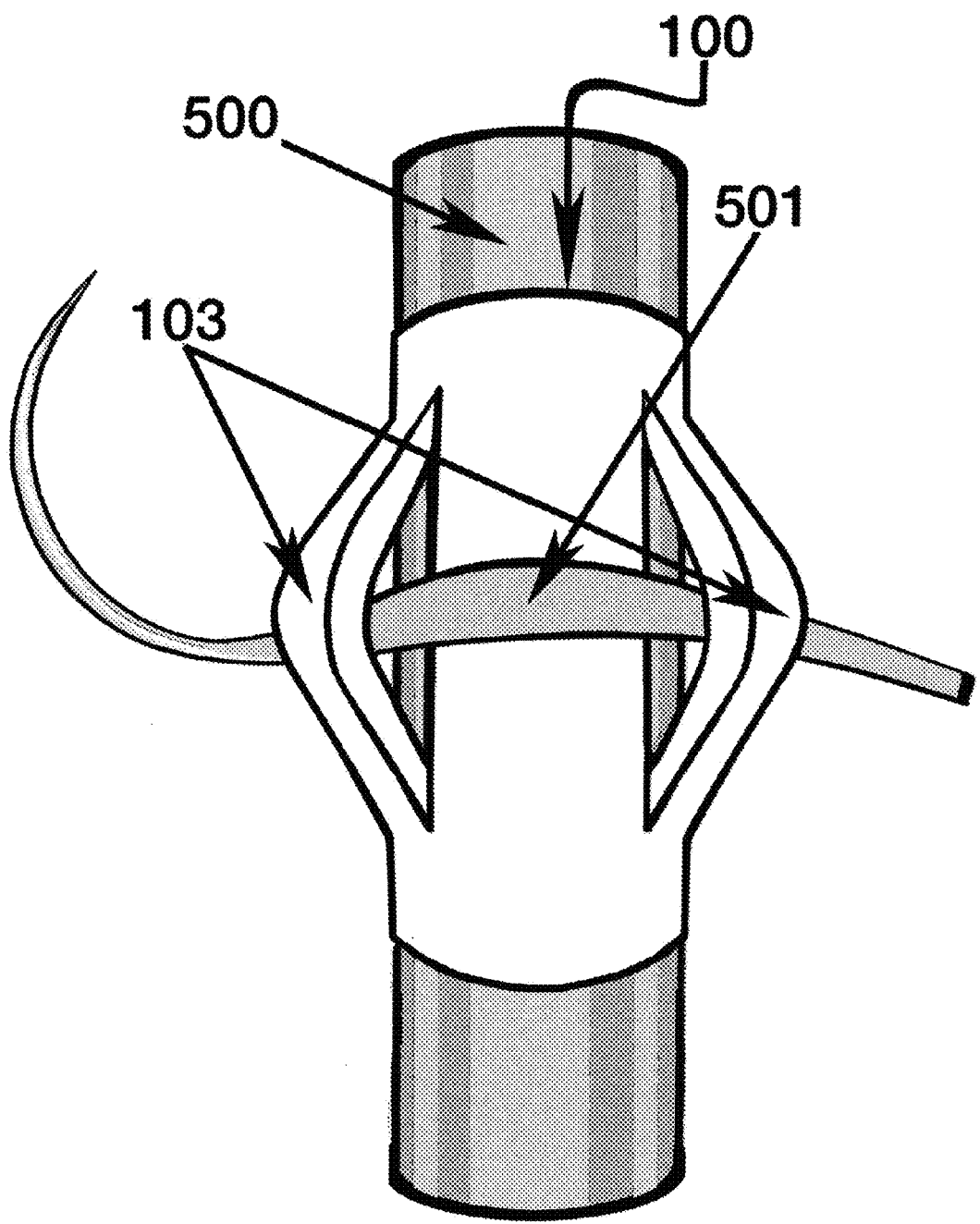
FIG. 5 is a perspective view of the medical tubing stabilizer wrapped around and adhered to tubing, showing the snap fasteners and interlocking lip in place.

FIG. 5 illustrates the device 100 in an exemplary application environment. As shown, the device 100 is wrapped about a portion of tubing 500. The anchors 103 are flexed open exposing a confined passage through which a stitch 501 is passed, confining the device 100 and hence the tubing 500.

In an embodiment of the invention as noted above, the device is produced as a cylindrical body sized to slide onto and fit securely on the tube of interest, rather than being formed as a sheet requiring a closure. The body contains a plurality of cuts, similar to the cuts 102 described above, with each pair of cuts forming a loop of material in the cylindrical body. Each such loop provides an attachment point to secure the cylindrical body and thus the tube of interest. The device may be formed with one such loop, or may have two or more such loops depending upon device application and size.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A tube retention device comprising:
   a flexible rectangular body sized to wrap around a tube of interest;
   a plurality of slits transverse to a primary axis of the flexible rectangular body to isolate one or more loops of material, attached at each end thereof to the remainder of the flexible rectangular body; and adhesion means to adhere the flexible rectangular body but not the one or more loops to the tube of interest when wrapped, such that the loops pop outward or may be pulled away from the tube of interest and stitched to an external body; further comprising one or more security features to lock one end of the flexible rectangular body to an opposite end of the flexible rectangular body when the flexible rectangular body is wrapped around the tube of interest.

2. The tube retention device according to claim 1, wherein the one or more loops of material comprise two loops.

3. The tube retention device according to claim 1, wherein the one or more security features include one or more snap caps at one end of the flexible rectangular body and one or mating holes in the opposite end of the flexible rectangular body.

4. The tube retention device according to claim 1, wherein the one or more security features include a hook and loop fastener portion at one end of the flexible rectangular body and a mating hook and loop fastener portion at the opposite end of the flexible rectangular body.

5. The tube retention device according to claim 4, wherein the hook and loop fastener portion at one end of the flexible rectangular body is on an opposite side of the device as the mating hook and loop fastener portion at the opposite end of the flexible rectangular body.

6. The tube retention device according to claim 1, wherein the tube of interest is a medical drainage tube and the external body is a human body.

7. The tube retention device according to claim 1, wherein the tube of interest is a nonmedical tube.

\* \* \* \* \*